(12) United States Patent
Gosiengfiao et al.

(10) Patent No.: US 6,612,998 B2
(45) Date of Patent: Sep. 2, 2003

(54) GUIDE WIRE WITH MARKER SLEEVE

(75) Inventors: Brandon Gosiengfiao, Temecula, CA (US); Douglas Gesswein, Temecula, CA (US); Wayne Cornish, Fallbrook, CA (US); Sharon Y. Wong, San Francisco, CA (US); Pablito Buan, Temecula, CA (US); Mark T. Richardson, Escondido, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 55 days.

(21) Appl. No.: 09/997,811

(22) Filed: Nov. 28, 2001

(65) Prior Publication Data

US 2003/0100848 A1 May 29, 2003

(51) Int. Cl.[7] ............................ A61B 5/00; A61M 25/00
(52) U.S. Cl. ............................................ 600/585
(58) Field of Search ................ 600/585, 433, 600/434, 435; 604/164.13, 528, 264

(56) References Cited

U.S. PATENT DOCUMENTS

| 4,989,608 A | 2/1991 | Ratner |
| 5,154,179 A | 10/1992 | Ratner |
| 5,174,302 A | 12/1992 | Palmer |
| 5,253,653 A | 10/1993 | Daigle et al. |
| 5,267,574 A | 12/1993 | Viera et al. |
| 5,458,615 A | 10/1995 | Klemm et al. |
| 5,507,768 A | 4/1996 | Lau et al. |
| 5,606,981 A | 3/1997 | Tartacower et al. |
| 5,817,017 A | 10/1998 | Young et al. |
| 5,891,112 A | 4/1999 | Samson |
| 6,132,388 A * | 10/2000 | Fleming et al. ............. 600/585 |
| 6,179,788 B1 | 1/2001 | Sullivan |
| 6,179,811 B1 | 1/2001 | Fugoso et al. |
| 6,241,690 B1 | 6/2001 | Burkett et al. |
| 6,428,489 B1 * | 8/2002 | Jacobsen et al. ............ 600/585 |

FOREIGN PATENT DOCUMENTS

WO  WO 01/36034 A2  5/2001

* cited by examiner

Primary Examiner—Max F. Hindenburg
Assistant Examiner—Brian Szmal
(74) Attorney, Agent, or Firm—Fulwider Patton Lee & Utecht, LLP

(57) ABSTRACT

An intracorporeal device such as a guide wire with an elongated core having a radiopaque and optionally MRI-compatible markers embedded in a polymer sleeve disposed on a distal section of the elongated core is disclosed. The marker sleeve may be secured to a tapered portion of the distal core section or a constant diameter portion of the distal core section. Individual markers may be formed by radiopaque ribbons, bands, or strips, or may be in the form of a helical coil.

24 Claims, 2 Drawing Sheets

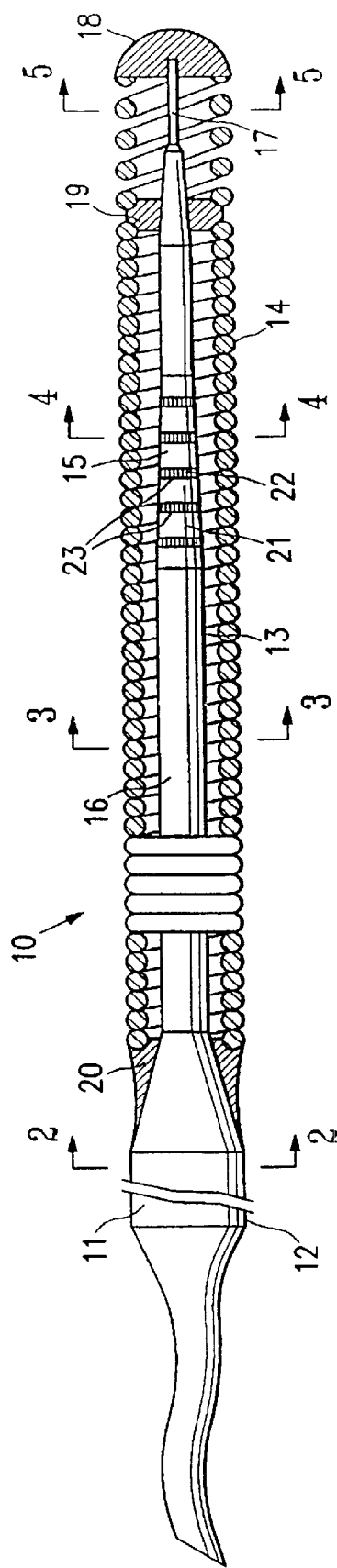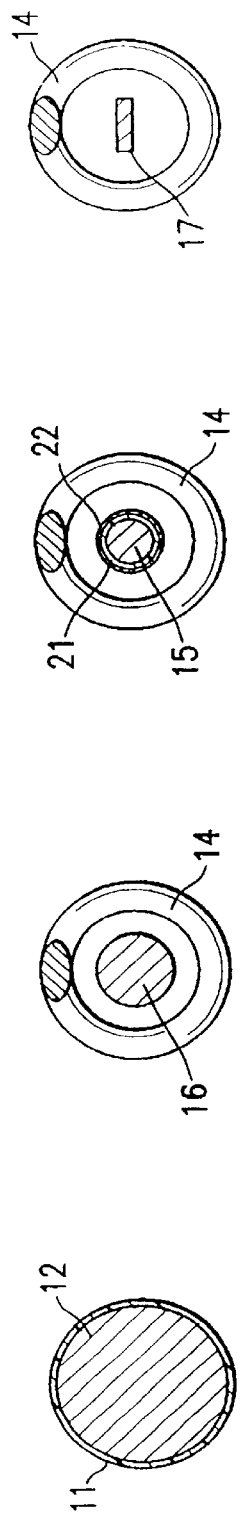

GUIDE WIRE WITH MARKER SLEEVE

BACKGROUND OF THE INVENTION

The present invention relates to the field of intravascular devices, and more particularly to a guide wire suitable for procedures such as angioplasty and/or stent deployment, and the like.

In percutaneous transluminal coronary angioplasty (PTCA) procedures a guiding catheter is first advanced in the patient's vasculature until the distal tip of the guiding catheter is seated in the ostium of a desired coronary artery. A guide wire is first advanced out of the distal end of the guiding catheter into the patient's coronary artery until the distal end of the guide wire crosses a lesion to be dilated. A dilatation catheter, having an inflatable balloon on the distal portion thereof, is advanced into the patient's coronary anatomy over the previously introduced guide wire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guide wire can be removed therefrom.

After such angioplasty procedures, there may be restenosis of the artery, i.e. reformation of the arterial blockage, which necessitates either another angioplasty procedure or some other method of repairing or strengthening the dilated area. To reduce the restenosis rate of angioplasty alone and to strengthen the dilated area, physicians now typically implant an intravascular prosthesis, generally called a stent, inside the artery at the site of the lesion. Stents may also be used to repair vessels having an intimal flap or dissection or to generally strengthen a weakened section of a vessel or to maintain its patency.

Stents are usually delivered to a desired location within a coronary artery in a contracted condition on a balloon of a catheter, which is very similar in many respects to a balloon angioplasty catheter, and the stent is expanded within the patient's artery to a larger diameter by inflating the balloon. After stent deployment, the balloon is deflated to facilitate removal of the catheter and the expanded stent is left in place within the artery at the site of the dilated lesion. See, for example, U.S. Pat. No. 5,507,768 (Lau et al.) and U.S. Pat. No. 5,458,615 (Klemm et al.), which are incorporated herein by reference. Instead of first using one balloon catheter to dilate the body lumen and a second balloon catheter to deploy the stent after the dilatation, the stent may be mounted on a balloon catheter and deployed at the same time the balloon is inflated to dilate the stenotic region.

In both of these procedures the physician has to make an estimate of the length of the stenotic region which is to be dilated or into which a stent is to be deployed in order to assess the length of the balloon to be used or the length of the stent to be deployed. Heretofore, it has been suggested to provide a variety of markers on the distal portion of the guide wire and/or catheters in order to measure the length of a stenosis or other anatomical region.

Many of these prior efforts involve providing various spacings between multiple radiopaque markers on the distal portion of the guide wire to allow the physician to make the length determination fluoroscopically with the guide wire in position within the artery and the markers traversing the stenotic region. For example, conventional approaches include using the helical coil commonly found at the distal end of the guide wire to include spaced apart radiopaque rings. Another approach is attaching radiopaque bands directly to the outside diameter of the guide wire core. The radiopaque bands are mounted to the core by adhesives or by use of shrink wrap covering the bands. Sometimes polymer sleeves are positioned in between the bands to function as spacers. However, the thick bands with shrink wrap would change the outside diameter of the core, and/or the stiffness of the wire. Accordingly, there is presently a need for an improved radiopaque marker arrangement for use with an intracorporeal device such as a guide wire and the like.

SUMMARY OF THE INVENTION

The present invention is generally directed to an intracorporeal device, such as a guide wire, for measuring a length of an anatomical feature or the distance between anatomical features within a patient's body, such as the length of stenosis within a patient's coronary arteries.

In one embodiment, the intracorporeal device comprises an elongated, solid core member having a proximal core section and a distal core section having at least one constant diameter portion and at least one tapered portion which tapers in the distal direction to smaller transverse dimensions; a continuous polymer sleeve secured to the distal core section having a plurality of radiopaque spaced apart marker edges embedded into the sleeve; and a flexible body disposed about and secured to the distal core section.

The intracorporeal device embodying features of the invention has a plurality of spaced apart marker edges or other location indicia on the distal portion of the device. The markers are observable (e.g., fluoroscopically) by the physician or other personnel while inside a patient during a procedure. In particular, the intracorporeal device is positioned within the patient's body with one of the marker edges being placed at or adjacent to a first intracorporeal location. The distance between the first intracorporeal location and a second intracorporeal location can then be determined by counting the marker edges and knowing the distance between the marker edges.

In one embodiment of the invention directed to guide wires, the polymer sleeve having a plurality of spaced apart marker sleeves is secured to a tapered or constant diameter portion of the distal core section. The flexible body includes a helical coil also at the distal core section of the guide wire. The marker containing sleeve may be positioned between coil segments, under coil segments, or at the end of a coil segment. The sleeve maybe heat shrunk onto the distal core section or it may be secured by adhesive or other suitable ways.

The marker containing sleeve may take several forms. In one form, the radiopaque marker or markers are provided on the exterior of a polymer sleeve. The markers may be applied in a variety of ways but plating is presently preferred. The entire exterior of the sleeve may be plated with a radiopaque material, and after plating the marker edges are formed by removing some of the plated material. Alternatively, a masking material may be placed on the exterior of the polymer sleeve to expose only those areas on the exterior which are to be plated. After the plating, the masking material may be removed.

In another embodiment of the marker containing sleeve, the marker or markers are embedded within the wall forming the polymer sleeve. The marker containing sleeve may be formed by disposing or otherwise applying an inner polymer layer onto the exterior of a mandrel of a desired shape. Individual ribbons of radiopaque material is wrapped around the inner polymer layer while still mounted on the mandrel. The continuous ribbon of radiopaque material is helically wrapped about the inner layer with a space between the individual turns to provide an appearance of a plurality of marker edges on one side of the sleeve. An outer polymer layer is applied to the partially completed sleeve on the mandrel to complete the sleeve construction. The inner and outer polymer layers may be heat shrunk, fused, or adhesively bonded to each other. If desired, the portion of the distal core section on which the sleeve is to be secured may be used as a mandrel so that the sleeve can be formed in situ.

In addition, the marker containing sleeve may be magnetic resonance imaging ("MRI") compatible. There would be no change in the overall construction of the marker containing sleeve, but materials in addition to common radiopaque marker materials would be needed, such as, NiTi and ternary alloys thereof. Paramagnetic materials such as gadolinium, chromium, nickel, copper, iron and manganese, and superparamagnetic materials could also be added for compatibility with MRI.

There are still other radiopaque materials that if added to the presently described marker containing sleeve would permit it to be MRI compatible. These radiopaque materials include, but are not limited to, platinum, iridium, gold, barium, bismuth, and other radiodense salts.

The location of the marker containing polymer sleeve on the core member depends upon the structure and use of the intracorporeal device, and particularly in the case where the intracorporeal device is a guide wire. To ensure that the distal position of the guide wire is not lost by movement of the guide wire during anatomical measurement, it is preferred to position the marker containing sleeve on the distal core section at a location spaced proximal to the distal end of the guide wire, preferably about 1 cm to about 20 cm, and more likely 3 to 5 cm as measured from the leading edge of the sleeve. The marker sleeve may be heat shrunk onto the core member, or secured to the core member in other suitable ways such as by adhesives and the like.

The guide wire or other intracorporeal device embodying features of the invention may be used in an intracorporeal procedure by introducing the distal portion of the guide wire or other device into the patient's body by a suitable procedure and advanced within the patient's body until the marker sleeve on the guide wire or other device is disposed at a desired intracorporeal location. The physician or other operator can fluoroscopically detect the markers on the marker sleeve and measure a length of anatomy by counting the number of marker edges and knowing the distance between the marker edges.

As a result, the use of the present invention marker containing polymer sleeve provides accurate placement of the marker edges for intracorporeal anatomical measurement with essentially no significant increase in the profile of the guide wire or other intracorporeal device. These and other advantages of the invention will be come more apparent from the following detailed description and the accompanying exemplary drawings.

BRIEF DESCRIPTION OF THE DRAWINGS

FIG. 1 is a side elevational view, partially in section, of a guide wire embodying features of the invention.

FIG. 2 is a transverse cross sectional view of the guide wire of FIG. 1 taken along line 2—2.

FIG. 3 is a transverse cross sectional view of the guide wire of FIG. 1 taken along line 3—3.

FIG. 4 is a transverse cross sectional view of the guide wire of FIG. 1 taken along line 4—4.

FIG. 5 is a transverse cross sectional view of the guide wire of FIG. 1 taken along line 5—5.

DETAILED DESCRIPTION OF THE PREFERRED EMBODIMENTS

Figure 6:
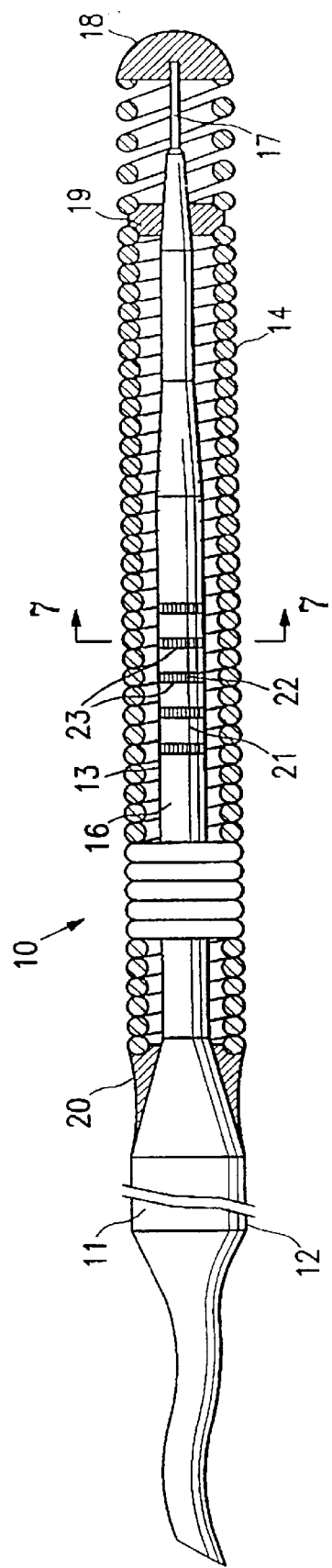
FIG. 6 is a side elevational view, partially in section, of an alternative embodiment guide wire embodying features of the invention.

The present invention is directed to an elongated intracorporeal device such as a guide wire, having radiopaque markers that are optionally magnetic resonance imaging ("MRI") compatible. The present invention construction of the sleeve is designed so that when mounted to the wire core, there is minimal increase in the outside diameter of the guide wire core and minimal interference with the flexibility of the wire core.

FIGS. 1–5 illustrate an embodiment of an intracorporeal guide wire 10 embodying features of the present invention. FIGS. 2–5 are cross sectional views taken along the length of the guide wire.

Specifically, FIG. 1 is a side elevational view of the guide wire 10 shown partially in a cross section. The guide wire 10 generally includes an elongated core member 11 with an elongated proximal shaft section 12, a distal shaft section 13 and a flexible helical coil 14 disposed about and secured to the distal shaft section 13. The distal shaft section 13 may have one or more tapered portions 15 and one or more constant diameter portions 16. Preferably, the tapered portion 15 decreases in its cross sectional area in the distal direction.

A flat shaping ribbon 17 extends from the distal end of the distal shaft section 13 to a rounded plug 18, which is formed when the distal end of the coil 14 is welded to the distal end of the flat shaping ribbon 17. The coil 14 is also optionally joined to the distal shaft section 13 at an intermediate location 19 and at its proximal end 20, usually by soldering, welding, bonding, or brazing.

In the illustrated embodiment best seen in FIGS. 1 and 4, a marker sleeve 21 is secured to the tapered portion 15. The marker sleeve 21 has at least one and more likely a plurality of radiopaque markers 22. The edges 23 of the markers 22 are spaced apart to allow the physician or other operator to fluoroscopically observe how many of the spaced marker edges 23 extend between the ends of the lesion or other anatomical feature in order to determine the length thereof. The spacing between the marker edges 23 preferably should be of a standard length unit so that the physician or other operating personnel can readily convert the number of marker edges 23 to a length measurement. The marker edges 23 may have suitable indicia adjacent thereto to provide the unit measurement in millimeters, inches, or the like.

Figure 7:
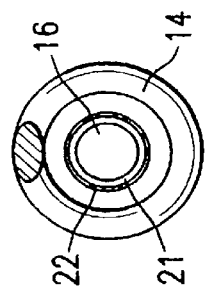
FIG. 7 is a transverse cross sectional view of the guide wire of FIG. 6 taken along line 7—7.

FIG. 6 is a side elevational view, shown partially in cross section, of another embodiment of the present invention guide wire 10. In this embodiment, the marker sleeve 21 with radiopaque markers 22 are located on a constant diameter portion 16 of the distal shaft section 13. FIG. 7 provides a cross sectional view taken along line 7—7 of FIG. 6 showing the marker sleeve 21 with radiopaque markers 22.

Figure 8:
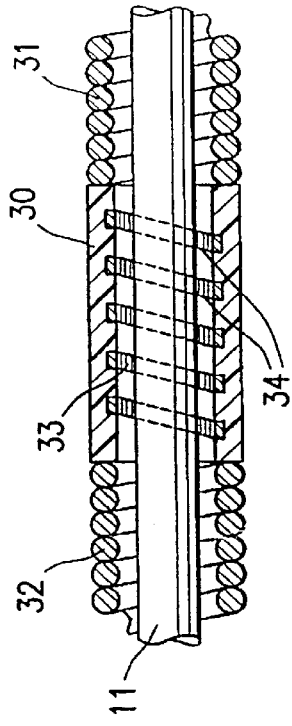
FIG. 8 is a partial side elevational view, shown in cross section, of an alternative guide wire construction embodying features of the invention.

FIG. 8 illustrates another embodiment in which the radiopaque marker sleeve 30 is disposed on a constant diameter portion of the core 11 wherein a distal tip coil 31 and an intermediate coil section 32 are butted up against the ends of the marker sleeve 30. The abutted joints are bonded, brazed, welded, or soldered, resulting in a smooth transition from coil to sleeve and back. Also, the radiopaque marker 33 is in the form of a helical coil embedded into the inside diameter of the polymer sleeve 30.

The marker edges 34 of the helical marker are preferably equally spaced as shown. The equal spacing is preferably at a distance of about 5 to about 30 mm to allow for the measurements of lesions throughout the patient's coronary arterial system. The marker or markers are preferably about 0.5 to about 3 mm in width to produce a relatively distinct and usable image when observed in a fluoroscope.

The marker or markers 33 may be formed individually in the form of radiopaque ribbons, discrete bands, or strips of foil wound into a helix that are embedded in the polymer marker sleeve 30. The cross sectional shape of the ribbon, band, or strip could be a rectangle, square, ovoid, circle or the like. The ribbons, bands, or foil strips may be fabricated from platinum, tantalum, or other radiopaque materials. A mandrel is used to set the shape of the polymer sleeve, and the radiopaque ribbons bands, or foil strips are then applied to the sleeve. Typically, if the sleeve 30 is used at the tapered portion 15, its profile is necked down on the mandrel with application of heat to match the taper in the core member.

If a radiopaque helical coil is used, the radiopaque coil can be used alone with the polymer sleeve, or it could be interlaced with a non-radiopaque, stainless steel coil acting as spacers in between each ring of the radiopaque coil. The combination is then embedded in the polymer sleeve. Such a construction of interlaced coils could be substituted in place of the intermediate coil section 32 shown in FIG. 8.

An optional covering layer of the sleeve may then be applied to cover over the radiopaque ribbons or coils. Furthermore, the polymer sleeve can be created by dipping or pushtrusion over the plated or flat ribbons of radiopaque material already attached to the core.

Alternatively, the markers 33 may be electroplated onto the polymer sleeve 30 using a radiopaque material such as gold, platinum, tin, and the like. On average, the plating is very thin in the range of about 0.0005 to 0.002 inch thick. If necessary, the plating may be as thin as about 0.0008 to 0.0018 inch thick. During the plating process, some portions of the exterior of the sleeve are masked while other portions are exposed. The masked areas prevent plating from coating non-marker regions.

In yet another plating process, the entire exterior of the marker sleeve may be plated with a radiopaque material such as gold. Afterward, the plating is selectively removed from non-marker portions of the exterior by laser ablation, chemical etching, mechanical abrasion or grinding, or the like. As mentioned earlier, the plating can be exposed or optionally be sandwiched in between layers of polymer material. As with the ribbon-embedded sleeve, the profile of a plated sleeve can be tapered by necking down the material on a mandrel while applying heat.

The marker containing sleeve 30 may be designed to be magnetic resonance imaging ("MRI") compatible. There would be no change in the overall construction of the marker containing sleeve, but materials in addition to common radiopaque marker materials would be needed, such as nickel-titanium (NiTi) and ternary alloys thereof. Paramagnetic materials such as gadolinium, chromium, nickel, copper, iron and manganese, and superparamagnetic materials such as iron oxide ($Fe_2O_3$, $Fe_3O_4$) could also be added for compatibility with MRI.

There are still other radiopaque materials that if added to the presently described marker containing sleeve would permit it to be MRI compatible. These radiopaque materials include, but are not limited to, platinum, iridium, gold, barium, bismuth, and other radiodense salts. Further information regarding MRI compatible materials and agents can be found in, for example, U.S. Pat. No. 5,817,017 (Young et al.), U.S. Pat. No. 5,154,179 (Ratner), and U.S. Pat. No. 4,989,608 (Ratner), whose contents are hereby incorporated by reference.

The location of the marker containing polymer sleeve on the core member depends upon the structure and use of the intracorporeal device, and particularly in the case where the intracorporeal device is a guide wire. To ensure that the distal position of the guide wire is not lost by movement of the guide wire during anatomical measurement, it is preferred to position the marker containing sleeve on the distal core section at a location spaced proximal to the distal end of the guide wire, preferably about 1 cm to 20 cm, and more likely about 3 cm to 5 cm as measured from the leading edge of the sleeve.

The polymer marker sleeve 30 can be secured, anchored, or attached to the core member 11 in a variety of ways. For example, the sleeve with marker or markers 33 may be heat shrinked to fit onto the core member 11. Other ways of securing the sleeve 30 include the use of adhesives, fusion bonding, soldering, and the like.

The material from which the sleeve is made is preferably a suitable thermoplastic polymer such as high density polyethylene (HDPE), polytetrafluorethylene (PTFE), polyethylene ethyl ketone (PEEK), polymethylmethacrylate (PMMA), polyimide, etc. For use with guide wires, the polymer layer has a thickness preferably ranging from about 0.0001 to 0.0015 inch. At such a small thickness, the effect on the crossing profile of the guide wire and the flexibility of the guide wire is negligible.

The present invention accommodates the majority of guide wire sizes with cores ranging from about 0.0009 to 0.035 inch. In various embodiments, the number of radiopaque marker bands using plating or flat ribbon on a polymer sleeve ranges from 5 to 15 with a preferred number of 7 to 12.

It will be apparent from the foregoing that, while particular forms of the invention have been illustrated and described, various modifications can be made without departing from the spirit and scope of the invention. Moreover, those skilled in the art will recognize that features shown in one embodiment of the invention may be utilized in other embodiments of the invention. To the extent not otherwise described herein, the materials and methods of construction and the dimensions of conventional intravascular guide wires may be employed with the intracorporeal device embodying features of the present invention. While the description of the invention is directed to embodiments for coronary applications, various modifications and improvements can be made to the invention without departing therefrom. Additionally, reference to the terms "members," "elements," "sections" and terms of similar import in the claims which follow shall not be interpreted to invoke the provisions of 35 U.S.C. §112 (paragraph 6)

unless reference is expressly made to the term "means" followed by an intended function.

What is claimed:

1. An intracorporeal device, comprising:
   an elongated, solid core member having a proximal core section and a distal core section having at least one constant diameter portion and at least one tapered portion which tapers in the distal direction to smaller transverse dimensions;
   a continuous polymer sleeve secured to the distal core section having a plurality of radiopaque spaced apart markers embedded into the polymer sleeve; and
   a flexible body disposed about and secured to the distal core section.

2. The intracorporeal device of claim 1, wherein the radiopaque markers are plated onto the polymer sleeve.

3. The intracorporeal device of claim 1, wherein the radiopaque markers include spaced apart turns of a radiopaque coil formed within a wall of the polymer sleeve.

4. The intracorporeal device of claim 1, wherein the polymer sleeve having a plurality of radiopaque markers is secured to a tapered portion of the distal core section.

5. The intracorporeal device of claim 1, wherein the polymer sleeve having a plurality of radiopaque markers is secured to the constant diameter portion of the distal core section.

6. The intracorporeal device of claim 1, wherein the flexible body disposed about and secured to the distal core section includes a helical coil.

7. The intracorporeal device of claim 6, wherein the flexible body includes two helical coil segments and the markers embedded in the polymer sleeve are positioned therebetween.

8. The intracorporeal device of claim 7, wherein the radiopaque markers include a structure selected from the group consisting of bands, foil strips, or helical coils.

9. The intracorporeal device of claim 1, wherein an intermediate coil is secured to the distal core section proximal to and abutting the polymer sleeve.

10. The intracorporeal device of claim 1, wherein the radiopaque markers are uniformly spaced along a length of the polymer sleeve.

11. The intracorporeal device of claim 1, wherein the radiopaque markers include a radiopaque coil interlaced with a relatively non-radiopaque coil.

12. The intracorporeal device of claim 1, wherein the polymer sleeve on he distal section of the guide wire is spaced at least about 3 to 5 cm from the distal end of the guide wire.

13. A guide wire for performing an intraluminal procedure, comprising:
    an elongated core having a proximal section and a distal section;
    a polymer sleeve secured to the distal core section, having a plurality of radiopaque spaced apart markers including an MRI compatible material embedded into a surface thereof; and
    a flexible body disposed about at least a portion of the distal section of the elongated core.

14. The guide wire of claim 13, wherein at least one of the plurality of the radiopaque markers includes an MRI compatible material selected from the group consisting of platinum, iridium, gold, barium, bismuth, or radiodense salts.

15. The guide wire of claim 13, wherein the MRI compatible material is selected from the group consisting of paramagnetic materials or superparamagnetic materials.

16. The guide wire of claim 13, wherein at least one of the plurality of radiopaque markers includes a material selected from the group consisting of nickel-titanium, or nickel-titanium alloyed with a ternary element.

17. The guide wire of claim 13, wherein the radiopaque markers include a structure selected from the group consisting of bands, foil strips, or helical coils.

18. The guide wire of claim 13, wherein at least one of the plurality of radiopaque markers includes a paramagnetic material selected from the group consisting of gadolinium, chromium, nickel, copper, iron, or manganese.

19. The guide wire of claim 13, wherein the polymer sleeve includes a material selected from the group consisting of high density polyethylene (HDPE), polytetrafluoroethylene (PTFE), polyethylene ethyl ketone (PEEK), polymethylmethacrylate (PMMA) or polyimide.

20. A method for providing an intracorporeal device for measuring an intraluminal location and for delivery of a therapeutic or diagnostic device, comprising:
    providing an elongated core member having a proximal core section and a distal core section having at least one constant diameter portion and at least one tapered portion;
    providing a polymer sleeve having a plurality of spaced apart MRI compatible markers embedded in the sleeve;
    disposing the polymer sleeve on the distal core section of the elongated core member; and
    providing a flexible body disposed about and secured to the distal core section.

21. The method of claim 20, wherein the method further comprises shrink wrapping the polymer sleeve onto the elongated core member.

22. The method of claim 20, wherein the method further comprises plating the polymer sleeve with a radiopaque material.

23. The method of claim 22, wherein the method further comprises selectively laser ablating the radiopaque plating.

24. The method at claim 20, wherein the method further comprises necking down thc sleeve to form a tapered profile.

* * * * *